United States Patent [19]

Schattschneider et al.

[11] Patent Number: 5,312,907

[45] Date of Patent: May 17, 1994

[54] GLYCOSIDURONIC ACIDS

[75] Inventors: Manfred Schattschneider, Niederzier-Ellen; Burkhard Weuste, Gummersbach; Hans J. Weissen, Kreuzau, all of Fed. Rep. of Germany

[73] Assignee: Akzo N.V., Netherlands

[21] Appl. No.: 957,312

[22] Filed: Oct. 5, 1992

[30] Foreign Application Priority Data

Oct. 8, 1991 [EP] European Pat. Off. ........ 91202608.5

[51] Int. Cl.$^5$ .................. C07H 15/04; C07H 15/10; C11D 1/66; C11D 1/04
[52] U.S. Cl. ............................ 536/18.6; 252/174.18; 536/4.1; 536/18.5; 536/120; 536/124; 536/126
[58] Field of Search ............... 536/18.6, 126, 4.1, 536/124, 18.5, 120

[56] References Cited

U.S. PATENT DOCUMENTS

| | | | |
|---|---|---|---|
| 2,472,168 | 6/1949 | Mehltretter et al. | 260/528 |
| 3,839,318 | 10/1974 | Mansfield | 260/210 |
| 4,393,203 | 7/1983 | Mao et al. | 536/124 |
| 4,732,696 | 3/1988 | Urfer | 252/174.17 |
| 4,889,925 | 12/1989 | Schmid et al. | 536/18.6 |
| 4,923,976 | 5/1990 | Arnaudis | 536/18.6 |
| 4,968,785 | 11/1990 | Moser et al. | 536/4.1 |
| 5,003,057 | 3/1991 | McCurry et al. | 536/4.1 |
| 5,166,337 | 11/1992 | Ripke | 536/126 |

FOREIGN PATENT DOCUMENTS

| | | |
|---|---|---|
| 132043 | 1/1985 | European Pat. Off. . |
| 326673 | 8/1989 | European Pat. Off. . |
| 415192 | 6/1991 | European Pat. Off. . |
| 886305 | 11/1952 | Fed. Rep. of Germany . |

OTHER PUBLICATIONS

Chem Abs 68:6927m No. 15 (Apr. 8, 1968) Coulon--Morelec "Synthesis of D-Glucuronic Acid.Lipid Glycosides".

*Primary Examiner*—Herbert J. Lilling
*Attorney, Agent, or Firm*—Ralph J. Mancini; Louis A. Morris

[57] ABSTRACT

Glycosiduronic acids, such as alkyl glycosiduronic acids or alkenyl glycosiduronic acids, which may be used in the preparation of surfactant compositions, such as detergents and cleansers, are prepared by reacting an oxidized mono-, oligo-, or polysaccharide with up to 10 monomer units with one or more fatty alcohols having 8–22 carbon atoms in the presence of a catalyst, preferably in bulk, and after acetalization removing the excess alcohol. Preferably the oxidized mono-saccharide used is glucuronic acid and/or glucuronic acid-3,6-lactone.

20 Claims, No Drawings

GLYCOSIDURONIC ACIDS

The present application for patent claims benefit under 35 U.S.C. 119, of European priority application Ser. No. 91202608.5, filed Oct. 8, 1991, which is hereby incorporated by reference.

FIELD OF INVENTION

The invention relates to a process for the preparation of glycosiduronic acids, such as alkyl glycosiduronic acids or alkenyl glycosiduronic acids, and the use thereof in the preparation of surfactant compositions, such as detergents and cleansers.

BACKGROUND OF THE INVENTION

For some time now it has not only been endeavored to use biodegradable substances in mass-produced articles such as detergents and cleansers in order to protect the environment, but also, since raw material sources such as crude oil or mineral coal are exhaustible, attempts are being made to prepare these compounds on the basis of regenerating raw materials.

Thus, e.g., alkyl glycosides, such as alkyl monosaccharides and alkyl oligosaccharides, according to U.S. Pat. No. 3,839, 318 are obtained from aldose sugars and higher alcohols and used as nonionic surfactants. Due to their limited solubility, the use of these products as mass-produced surfactants is subject to restrictions. Efforts have been made to increase the hydrophilic nature of these substances by oxidizing such alkyl glucosides to alkyl glucuronic acids, as is described, e.g., in EP-OS 326 673. Because of their hydrophilic and hydrophobic structural elements these compounds are highly suitable for use as detergents and cleansers both by themselves and in combination with other surfactants. A drawback to this preparative process is that a comparatively large amount of catalyst is needed, that despite the use of large amounts of catalyst the yield is unsatisfactory, and that, furthermore, long reaction periods are required.

Therefore, there is still need for an improved process for the preparation of glycosiduronic acids such as alkyl glycosiduronic acids or alkenyl glycosiduronic acids.

SUMMARY OF THE INVENTION

The invention generally relates to a process for the preparation of glycosiduronic acids which does not have the drawbacks inherent with prior art processes yet, has above all economic advantages and operates with good yields. More particularly, the present invention contemplates a process for the preparation of glycosiduronic acids having a) at least one glycoside unit carrying a carboxyl function directly attached to the glycoside ring, and b) at least one glycoside unit carrying an acetalically bound hydrocarbon group with 8-22 carbon atoms, the unit defined under a) and b) optionally being the same unit, characterized in that an oxidized mono-, oligo-, or polysaccharide with up to 10 monomer units is reacted with one or more fatty alcohols having 8-22 carbon atoms in the presence of a catalyst, and after acetalization the non-reacted alcohol is removed.

DETAILED DESCRIPTION OF THE INVENTION

The present invention generally relates to a process for the preparation of glycosiduronic acids, such as alkyl glycosiduronic acids or alkenyl glycosiduronic acids, having a) at least one glycoside unit carrying a carboxyl function directly attached to the glycoside ring, and b) at least one glycoside unit carrying an acetalically bound hydrocarbon group, such as an alkyl or alkenyl group with 8-22 carbon atoms, the unit defined under a) and b) optionally being the same unit, which is characterized in that an oxidized mono-, oligo-, or polysaccharide with up to 10 monomer units is reacted with one or more fatty alcohols having 8-22 carbon atoms in the presence of a catalyst, preferably in bulk, and after acetalization the non-reacted alcohol is removed. The use of a stoichiometric excess of the fatty alcohol is preferred. Preferably, the catalysts used are acid catalysts, more particularly p-toluene sulphonic acid, sulphosuccinic acid, methane sulphonic acid and C14/16-olefin sulphonic acid. It is advantageous to use 1-6, preferably 1-3 moles of fatty alcohol per mole of oxidized saccharide.

In a preferred embodiment of the process according to the invention the oxidized saccharide is reacted, in a first step, with an excess of the fatty alcohol, and after the first step, further oxidized saccharide is added in one or more portion. After acetalization the excess fatty alcohol can be removed at best by one of the following two general procedures.

The first procedure comprises the distillation of the excess alcohol, more particularly the distillation of the alcohol from thin films of the reaction mixture at a temperature of 100° to 190° C., preferably 150°-180° C., preference being given in this procedure to molecular distillation.

The second procedure comprises a process which may be called a liquid/solid separation process. Herein the reaction mixture is treated with an organic solvent, preferably lower aliphatic alcohols such as ethanol or isopropanol, containing a base thus precipitating the alkyl glycosiduronic acid as salt. The excess fatty alcohol remains in solution. Whereas the distillation is preferred at higher fatty alcohol/oxidized saccharide ratios, the liquid/solid separation process is preferably used at lower fatty alcohol/oxidized saccharides ratios. In one especially advantageous embodiment of the process according to the invention the oxidized monosaccharide used is glucuronic acid and/or glucuronic acid-3,6-lactone. The present invention further contemplates the use of the glycosiduronic acids obtained by the process(es) described hereinbefore for the preparation of surfactant compositions, more particularly detergents and cleansers.

The glycosiduronic acids have as their bases monosaccharides or polysaccharides containing up to 10 monomer units, which have at least one glycoside unit carrying a carboxyl function — optionally in the form of a lactone — that is directly attached to the sugar ring. The basis of these carboxyl-functional mono-, oligo-, and polysaccharides is formed, in its turn, by mono-, oligo-, and polysaccharides of which the glycoside units are present in the α- or β-form 1,2-, 1,3-, 1,4-, or 1,6-linked. These saccharides may be composed of hexoses which in the non-oxidized form carry primary glycosidic hydroxyl groups, such as glucose, galactose, and mannose. The preferred component is glucose.

The preferably obtained glycosiduronic acids contain at least one glucuronic acid unit of the structure

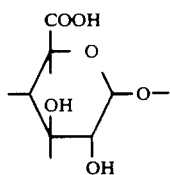

In addition, also other glycoside units, more particularly glycoside units of the structure

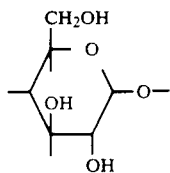

may be comprised. The hydrocarbon group is acetalically bond and preferably lies in the structure

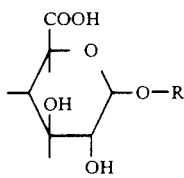

wherein R = C8-22 alkyl.

Alternatively, the acetalically bound hydrocarbon group may be present in the form of other glycoside units, more particularly glycoside units of the structure

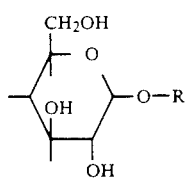

Particularly preferred glycosiduronic acids are alkyl glucuronic acids of the structure

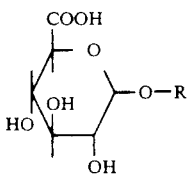

wherein R = C8-18 alkyl.

The glycosiduronic acids are prepared by reacting the described oxidized mono-, oligo-, or polysaccharides with a fatty alcohol in the presence of a catalyst at elevated temperature. It is also possible for mixtures to be used.

For acetalizing, preferable use is made of oxidized monosaccharides, more particularly glucuronic acid and glucuronic acid-3,6-lactone.

The fatty alcohols contain an alkyl group with 8-22 carbon atoms. In addition, the alkyl group may be linear or branched. In the primary reaction fatty alcohols are employed in stoichiometric excess, more particularly in an amount of 3-6 moles (calculated on 1 mole of oxidized saccharide). With regard to additional dosage of oxidized saccharide the overall molar ratio of fatty alcohol and oxidized saccharide is about 1-6:1.

Instead of an alkyl group some other, e.g. unsaturated hydrocarbon group, such as an alkenyl group, may be present. As an example the oleyl group is mentioned.

By fatty alcohols are meant both alcohols of natural origin and synthetically prepared alcohols. The alcohol's hydrocarbon group may carry substituents, e.g. hydroxyl groups; alternatively, the hydrocarbon chain may be interrupted by heteroatoms, such as oxygen.

Suitable as catalyst are conventional acetalization catalysts, such as p-toluene sulphonic acid, sulphosuccinic acid, and sulphuric acid. The catalysts are added in an amount of 0.2-5 wt. % (calculated on oxidized glycoside), preferably in an amount of 0.5-2 wt. %.

The reaction is carried out at a temperature of 70°-110° C., preferably 80°-100° C. To accelerate the reaction the removal of the formed water is supported by applying a vacuum. If the reaction affords additional dosage of oxidized saccharide each further portion can be added when the previous portion has been dissolved in the reaction mixture. The reaction is proceeded for about 0.5-3 hours, preferably 1-2 hours, after the last portion of oxidized saccharide has been dissolved. The excess fatty alcohol can be removed by vacuum distillation, preferably by distilling the excess alcohol from thin films of the reaction mixture at a temperature of 100°-190° C., more particularly 150°-180° C. The removal by distillation is preferably applied to reaction mixtures with higher fatty alcohol/oxidized saccharide ratios.

By treatment with bases, such as alkali metal hydroxides, ammonia, and amines, the thus prepared glycosiduronic acids can be converted to their water-soluble salts.

Alternatively, the reaction mixture can be treated with an organic solvent, such as ethanol and isopropanol containing a base. The organic solvent dissolves the fatty alcohol and the base forms the corresponding salt of the glycosiduronic acid which precipitates from the organic phase.

The glycosiduronic acid salts show surface active properties and can be used for the preparation of detergents and cleansers. They can be combined with other surfactants and with other substances used in the preparation of detergents and cleansers.

The invention will be further elucidated with reference to the following non-limiting examples.

EXAMPLE 1

790 g of a C12/14 fatty alcohol mixture is charged to a distillation apparatus and heated to 90° C. Subsequently, 1,8 g of p-toluene sulphonic acid is added. After the catalyst has dissolved, 176 g of finely powdered glucuronic acid-3,6-lactone is added and a water jet vacuum is applied. After 2.5 hours the glucuronic acid lactone has dissolved.

Stirring is continued for another hour. After this time the reaction water is virtually completely separated.

Then the reaction mixture is subjected to molecular distillation in an oil pump vacuum at 170° C. to separate the excess fatty alcohol.

EXAMPLE 2

395 g of a C12/14-fatty alcohol mixture is charged to a distillation apparatus and heated to 95° C. while stirring. Then, 0.9 g of p-toluene sulphonic acid is thereafter added. After the catalyst has dissolved, 88 g of finely powdered glucuronic acid-3,6-lactone are added and a water jet vacuum is applied. After about 2 hours the glucuronic acid-3,6-lactone has dissolved. Then, the water jet vacuum is interrupted and another portion comprising 88 g of finely powdered glucuronic acid-3,6-lactone and 0.9 g p-toluene sulphonic acid is added. After 1–1.5 hours the additional portion lactone has dissolved. The last step is repeated once more.

After a subsequent stirring of about 1 hour the reaction water is virtually completely separated. The reaction mixture is poured within 30 min into a well-stirred solution of 80 g sodium hydroxide in 3 l ethanol of 60° C. After complete addition, the reaction mixture is refluxed for 30 min. The suspension is cooled, and filtered at room temperature. The filter cake is washed with ethanol and dried in vacuum. The sodium salt of C12–14-alkylglucuronic acid is recovered as yellowish powder (bleachable, e.g. by means of hydrogen peroxide).

It was particularly surprising that with the process according to the invention it was not only possible to reduce the reaction times in comparison with the acetalization of non-oxidized saccharides, but also that good yields were obtained. It is also possible to work at lower temperatures. This difference renders the process considerably more economical. The raw materials used are renewable and the biodegradability of the products is very good. The products are eminently suited to be used for the preparation of detergents and cleansers.

If the amounts of fatty alcohol required for acetalizing glucose are compared with the amounts of fatty alcohol needed in the process according to the invention for the acetalization of equal molar quantities of glucuronic acid or glucuronic acid lactone, a notable reduction in the amount of alcohol needed will result in the case of the process according to the invention.

We claim:

1. A process for the preparation of glycosiduronic acids having
    (a) at least one glycoside unit carrying a carboxyl function directly attached to the glycoside ring, and
    (b) at lest one glycoside unit carrying an acetalically bound hydrocarbon group with 8-22 carbon atoms, the unit defined under a) and b) optionally being the same unit,
characterized in that an oxidized mono-, oligo-, or polysaccharide with up to 10 monomer units which has at least one glycoside unit carrying a carboxyl function is reacted with one or more fatty alcohols having 8-22 carbon atoms in the presence of a catalyst, and after acetalization the non-reacted alcohol is removed and the glycosiduronic acid product is recovered.

2. The process according to claim 1, wherein a stoichiometric excess of the fatty alcohol is used.

3. The process according to claim 1, wherein the reaction is carried out in bulk.

4. The process according to claim 1, wherein said catalyst is an acid catalyst.

5. The process according to claim 4, wherein said catalyst used is selected from the group consisting of p-toluene sulphonic acid, methane sulphonic acid, C14/16-olefinsulphonic acid and sulphosuccinic acid.

6. The process according to claim 1, wherein 1-6 moles of alcohol are employed per mole of oxidized saccharide.

7. The process according to claim 6, wherein 1-3 moles of alcohol are employed per mole of oxidized saccharide.

8. The process of claim 1, wherein as a first step the oxidized saccharide is reacted with an excess of fatty alcohol and after the first step a further oxidized saccharide is added in one or more portions.

9. The process according to claim 8, wherein in said first step 3-6 moles of fatty alcohol per mole of oxidized saccharide are employed.

10. The process according to claim 9, wherein in said first step 3-4 moles of fatty alcohol per mole of oxidized saccharide is employed.

11. The process according to claim 1, wherein the non-reacted alcohol is removed by means of distillation.

12. The process according to claim 11, wherein the non-reacted alcohol is removed by distillation from thin films of the reaction mixture at a temperature of 100° to 190° C.

13. The process according to claim 12, wherein the distillation is carried out at a temperature of 150°–180° C.

14. The process according to claim 13, wherein the non-reacted alcohol is removed by molecular distillation.

15. The process according to claim 1, wherein the reaction mixture is treated with an organic solvent containing a base resulting in the precipitation of alkyl glycosiduronic acid as a salt.

16. The process according to claim 15, wherein said solvent is a lower aliphatic alcohol.

17. The process according to claim 16, wherein said lower aliphatic alcohol is selected from the group consisting of ethanol and isopropanol.

18. The process according to claim 1, wherein the oxidized monosaccharide is selected from the group consisting of glucuronic acid, glucuronic acid-3,6-lactone, and mixtures thereof.

19. The process according to claim 1, wherein said hydrocarbon group is an alkyl group.

20. The process according to claim 1, wherein said hydrocarbon group is an alkenyl group.

* * * * *